United States Patent [19]
Hörsch et al.

[11] Patent Number: 5,962,275
[45] Date of Patent: Oct. 5, 1999

[54] METHOD FOR THE ENZYMATIC GALACTOSYLATION OF MONOSACCHARIDES AND OLIGOSACCHARIDES

[75] Inventors: Brigitte Hörsch, Hofheim; Andreas Seiffert-Störiko; Rüdiger Marquardt, both of Frankfurt, all of Germany; Astrid Zervosen, Welkenraedt, Belgium; Lothar Elling, Aachen; Maria Regina Kula, Niederzier-Hambach, both of Germany

[73] Assignee: Hoechst Aktiengesellschaft, Frankfurt, Germany

[21] Appl. No.: 08/952,197

[22] PCT Filed: May 2, 1996

[86] PCT No.: PCT/EP96/01828

§ 371 Date: Feb. 13, 1998

§ 102(e) Date: Feb. 13, 1998

[87] PCT Pub. No.: WO96/35801

PCT Pub. Date: Nov. 14, 1996

[30] Foreign Application Priority Data

May 12, 1995 [DE] Germany .............. 195 16 952

[51] Int. Cl.$^6$ ............... C12P 19/18; C12P 19/12; C12P 19/24; C12P 19/14
[52] U.S. Cl. ............... 435/97; 435/100; 435/101; 435/94; 435/99
[58] Field of Search ............... 435/97, 100, 101, 435/94, 99

[56] References Cited

U.S. PATENT DOCUMENTS 5,750,389  5/1998  Elling et al. ............... 435/193

FOREIGN PATENT DOCUMENTS

94/01540  1/1994  WIPO.

OTHER PUBLICATIONS

Elling et al, Glycobiology 3(4):349–355, 1993.
Wong et al, J. Org. Chem 57:4343–4344, 1992.
Ray et al, Biochem. Biophys. Res. Comm. 60(3):1081–1089, (1974).
Kragl et al, Tetrahedron:Asymmetry 4(6):1193–1202 (1993).

*Primary Examiner*—Francisco Prats
*Attorney, Agent, or Firm*—Frommer Lawrence & Haug LLP

[57] ABSTRACT

The invention relates to an improved process for enzymically galactosylating monosaccharides and oligosaccharides, with in-situ regeneration of the nucleotide sugar (or of the nucleoside diphosphate sugar), in the presence of sucrose synthase, β-1-4-galactosyl transferase and uridine diphosphate-glucose 4'-epimerase, (UDP-glucose 4'-epimerase), in which process the uridine diphosphate-glucose 4'-epimerase is reactivated with a ketosugar derivative.

7 Claims, 11 Drawing Sheets

| 1 | PHOSPHOGLUCOMUTASE | 4 | UDP-GLc 4 - EPIMERASE |
| 2 | UDP-GLc PYROPHOSPHORYLASE | 5 | GALACTOSYL TRANSFERASE |
| 3 | PYROPHOSPHATASE | 6 | PYRUVATE KINASE |

| 1 | PHOSPHOGLUCOMUTASE | 4 | UDP-GLc 4 - EPIMERASE |
| 2 | UDP-GLc PYROPHOSPHORYLASE | 5 | GALACTOSYL TRANSFERASE |
| 3 | PYROPHOSPHATASE | 6 | PYRUVATE KINASE |

1   SUCROSE SYNTHASE
2   UDP-Gal EPIMERASE
3   B-1-4-Gal TRANSFERASE (1): CONVERSION AFTER 12 h (2): CONVERSION 8 h AFTER ADDING NEW SUBSTRATE (3): COVERSION AFTER A FURTHER 14 h AFTER ADDING 175 mU OF EPIMERASE

ACTIVITY OF THE EPIMERASE AFTER AN INCUBATION TIME
OF 8 h IN THE PRESENCE OF

A: BUFFER SOLUTION A
B: BUFFER SOLUTION A, 0.1 mM UMP
C: BUFFER SOLUTION B
D: BUFFER SOLUTION B, 0.1 mM UMP

A: 20 mM 6-DEOXYGLUCOSONE
B: 20 mM GALACTOSONE
C: 20 mM ALLOSONE
D: 20 mM GLUCOSONE
E: 0.1 mM dTDP-6-DEOXY-D-XYLO-4-HEXULOSE
F: 1 mM dTDP-6-DEOXY-D-XYLO-4-HEXULOSE
G: 0.1 mM dUDP-6-DEOXY-D-XYLO-4-HEXULOSE
H: mM dUDP-6-DEOXY-D-XYLO-4-HEXULOSE

REACTIVATION WITH G: 0.1 mM dUDP-6-DEOXY-D-XYLO-4-HEXULOSE, AND WITH H: 1 mM dUDP-6-DEOXY-D-XYLO-4-HEXULOSE

METHOD FOR THE ENZYMATIC GALACTOSYLATION OF MONOSACCHARIDES AND OLIGOSACCHARIDES

CROSS-REFERENCE TO RELATED APPLICATION

This application claims priority to German Application No. P 195 16 952.2 filed May 12, 1995, and is a 371 of International Application No. PCT/EP96/01828 filed May 2, 1996, incorporated herein by reference.

BACKGROUND OF THE INVENTION

1. Field of the Invention

The invention relates to an improved process for enzymically galactosylating monosaccharides and oligosaccharides, with in-situ regeneration of the nucleotide sugar (or of the nucleoside diphosphate sugar), in the presence of sucrose synthase, β-1-4-galactosyl transferase and uridine diphosphate-glucose 4'-epimerase (UDP-glucose 4'-epimerase).

2. Description of the Related Art

Enzymic syntheses of N-acetyllactosamine (LacNAc) and its derivatives using β-1-4-galactosyl transferase (GalT) [EC 2.4.1.38] have been known for a long time (C. H. Wong et al.: J. Am. Chem. Soc. 118, 8137 (1991), J. Org. Chem. 57, 4343 (1992)). Wong et al. (FIGS. 1 and 2) developed LacNAc syntheses which involved in-situ regeneration of UDP-glucose, which made it unnecessary to use stoichiometric quantities of the expensive nucleotide sugars, but which nevertheless required 6 different enzymes.

As compared with the previously known cycles, the LacNAc cycle (FIG. 3) proposed by Elling et al. (Glycobiology 3, 349 (1993), DE 42 21 595 C1)), represents an improvement in so far as only three enzymes, i.e. rice sucrose synthase, β-1-4-galactosyl transferase and UDP-glucose 4'-epimerase, instead of six still have to be used for synthesis. The disaccharides which are synthesized are the starting compounds for further reactions with different transferases, e.g. sialyl transferases and fucosyl transferases. The target products for these enzyme syntheses are sialyl Lewis X and its derivatives (Ichikawa et al. J. Am. Chem. Soc. 114, 9283 (1992)), whose importance in cell/cell recognition is the subject of intensive research (DeFrees et al. J. Am. Chem. Soc. 117, 66 (1995)).

Sucrose synthase [EC 2.4.1.13] (S. Syn.), which is a glycosyl transferase which is widely distributed in plants, in particular, and whose function as a catalyst for forming nucleotide sugars in plant metabolism has been summarized by Avigad (in Loewus et al. (Eds) Encyclopedia of Plant Physiology New Series Vol. 13A, Carbohydrates I, Intracellular Carbohydrates, Springer Verlag, Berlin, 217–347, 1982) is suitable for synthesizing nucleotide sugars such as UDP-Glc, dTDP-Glc, ADP-Glc, CDP-Glc and GDP-Glc (Elling et al. Glycobiology 3, 349 (1993)). The purification of rice sucrose synthase, and its use for the in-situ regeneration of UDP-glucose, have been described by Elling at al. (DE 42 21 595 C1, Biotechnol. Appl. Biochem. 21, 29 (1994)). The rice enzyme is a homotetrameric protein having a molecular weight of 362 kDa. The enzyme has already been used by Zervosen et al. (Angew. Chem. 106, 592 (1994)) for the preparative synthesis of dTDP-Glc in an enzyme membrane reactor (EMR) and employing dTDP as the starting compound.

The central enzyme for LacNAc synthesis is β-1-4-galactosyl transferase, which transfers UDP-galactose to N-acetylglucosamine. This results in N-acetyllactosamine. A number of other monosaccharides and oligosaccharides can be used as acceptors.

The third enzyme in the Elling at al. (DE 42 21 595 C1) LacNAc cycle is UDP-glucose 4'-epimerase [E.C. 5.1.3.2]. The Saccharomyces cerevisiae enzyme, which can be purchased from Sigma, is composed of two subunits to which a molecule of NAD is firmly, but not covalently, bound (Fucusawa et al. J. Biol. Chem. 255, 2705 (1980)). This enzyme does not therefore require any externally added cofactor. The properties of the *E. coli* and yeast epimerases have been described by Frey et al. (in D. Dolphin et al (Eds.) Pyridine Nucleotide Coenzymes: Chemical, Biochemical and Medicinal Aspects, Vol. 2B, Wiley, N.Y. 462–511).

The epimerization is effected by the UDP-glucose being oxidized to the UDP-4'-ketopyranose and the latter subsequently being reduced to the C4' epimer of the starting compound (FIG. 4).

The epimerase is reductively inactivated in the presence of specific sugars, in the presence of UMP or UDP and by the substrates UDP-glucose and UDP-galactose (Carmenes et al. Yeast 2, 101 (1986) Nelestuen et al., J. Biol. Chem. 4, 7533 (1971)). By binding to the enzyme, uridine nucleotides, such as UMP, induce a conformational change which increases the reactivity of bound NAD to reducing substances. The epimerase-NADH which is subsequently formed exhibits only 10–15% of the activity of the native enzyme (Kalckar et al., Proc. Nat. Ac. Sci. 65, 1113 (1970)).

Owing to the epimerase being inactivated, the previously described enzymic syntheses of LacNAc, involving in-situ regeneration of the nucleotide sugars, only achieve low cycle numbers and, particularly in the case of unnatural substrates, only unsatisfactory yields. In order to increase the yields of disaccharide or oligosaccharide it is essential to meter in further epimerase repeatedly, thereby making the synthesis uneconomical.

OBJECT OF THE INVENTION

By contrast, the object of the present invention is to make available an economic process for enzymically synthesizing disaccharides and oligosaccharides, in which process inactivation of the UDP-glucose 4'-epimerase is avoided.

SUMMARY OF THE INVENTION

The object is achieved by a process for enzymically galactosylating monosaccharides and oligosaccharides, with in-situ regeneration of the nucleotide sugar, in the presence of sucrose synthase, β-1-4-galactosyl transferase and uridine diphosphate-glucose 4'-epimerase, wherein a ketosugar or a ketosugar derivative is added to the reaction mixture as an activator of uridine diphosphate-glucose 4'-epimerase.

A deoxynucleoside diphosphate-ketosugar, preferably deoxyuridine diphosphate-6-deoxy-D-xylohexulose or deoxythymidine diphosphate-6-deoxy-D-xylohexulose, is a particularly suitable activator.

A ketosugar is also a suitable activator. Preference is given to using 6-deoxyglucosone, galactosone, allosone or glucosone.

DETAILED DESCRIPTION OF THE INVENTION

In the novel process, the concentration of the activator in the reaction mixture is from 0.01 to 20 mM, preferably from 0.1 to 1 mM.

The process according to the present invention can also be performed as a repetitive-batch process in an ultrafiltration cell.

When the novel process is used, the UDP-glucose 4'-epimerase is reactivated without the activity of the other enzymes, i.e. sucrose synthase and β-1-4-galactosyl transferase, being impaired.

Figure 1:
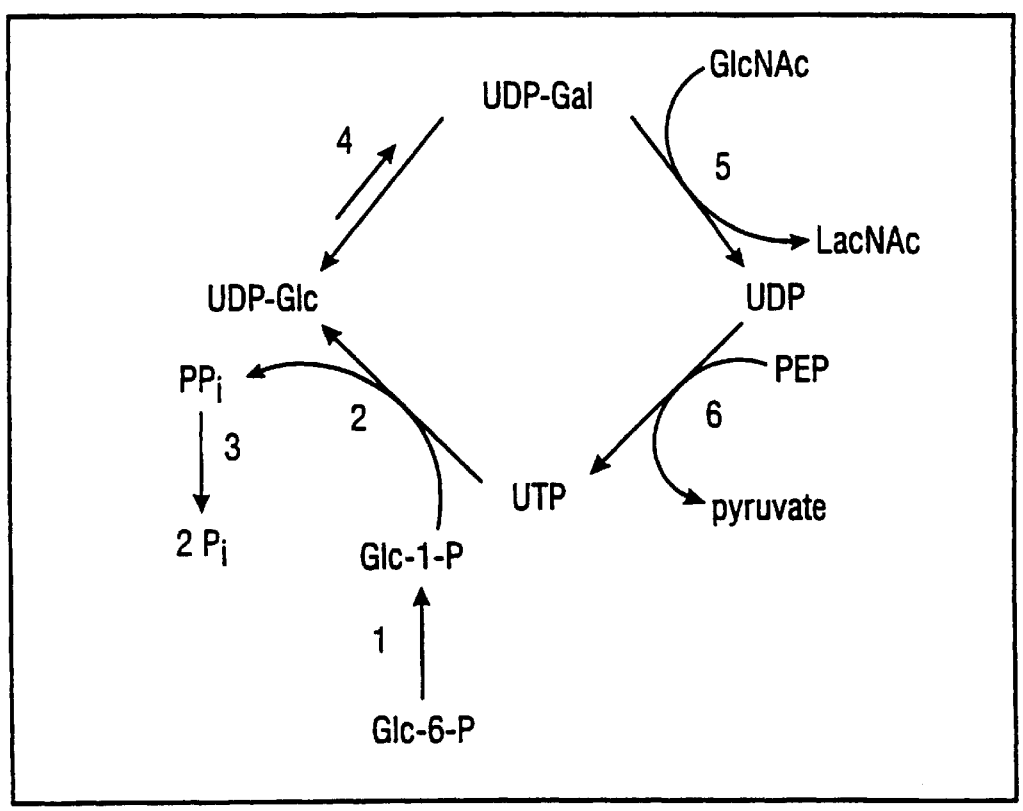
FIG. 1 shows a schematic drawing of the enzymic synthesis of N-Acetyllactosamine according to Wong et al.
Figure 2:
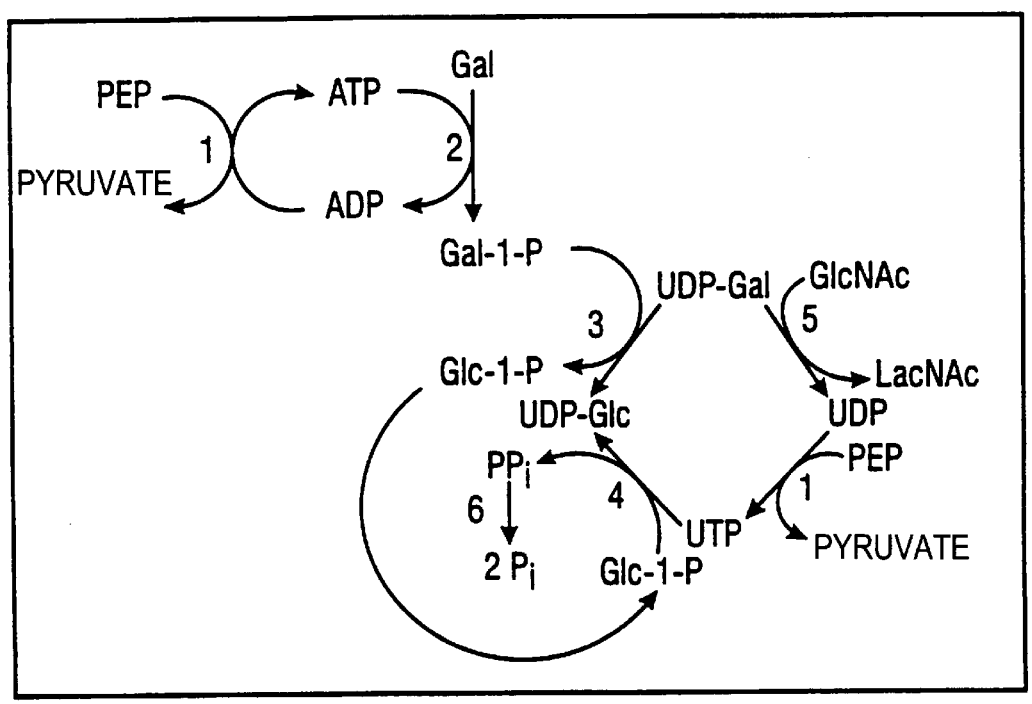
FIG. 2 shows a schematic drawing of the enzymic synthesis of N-Acetyllactosamine according to Wong et al.
Figure 3:
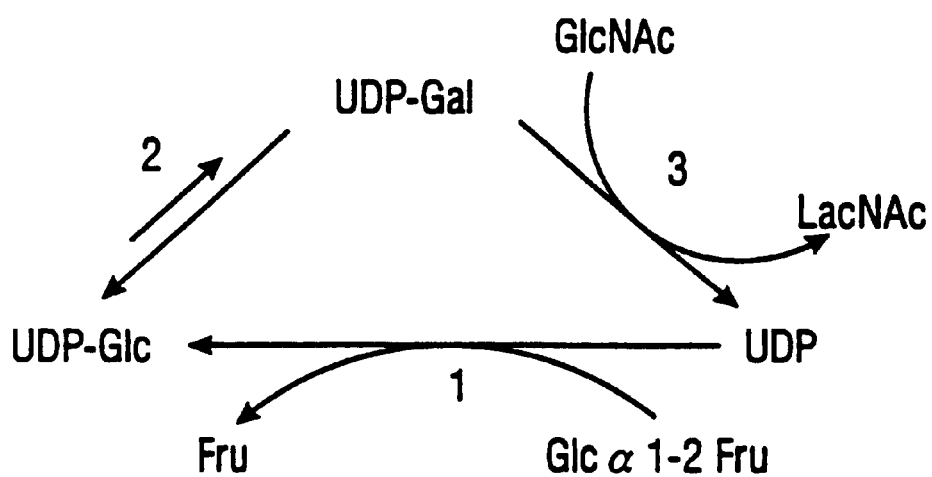
FIG. 3 shows a schematic drawing of the enzymic synthesis of N-Acetyllactosamine according to Elling et al.
Figure 4:
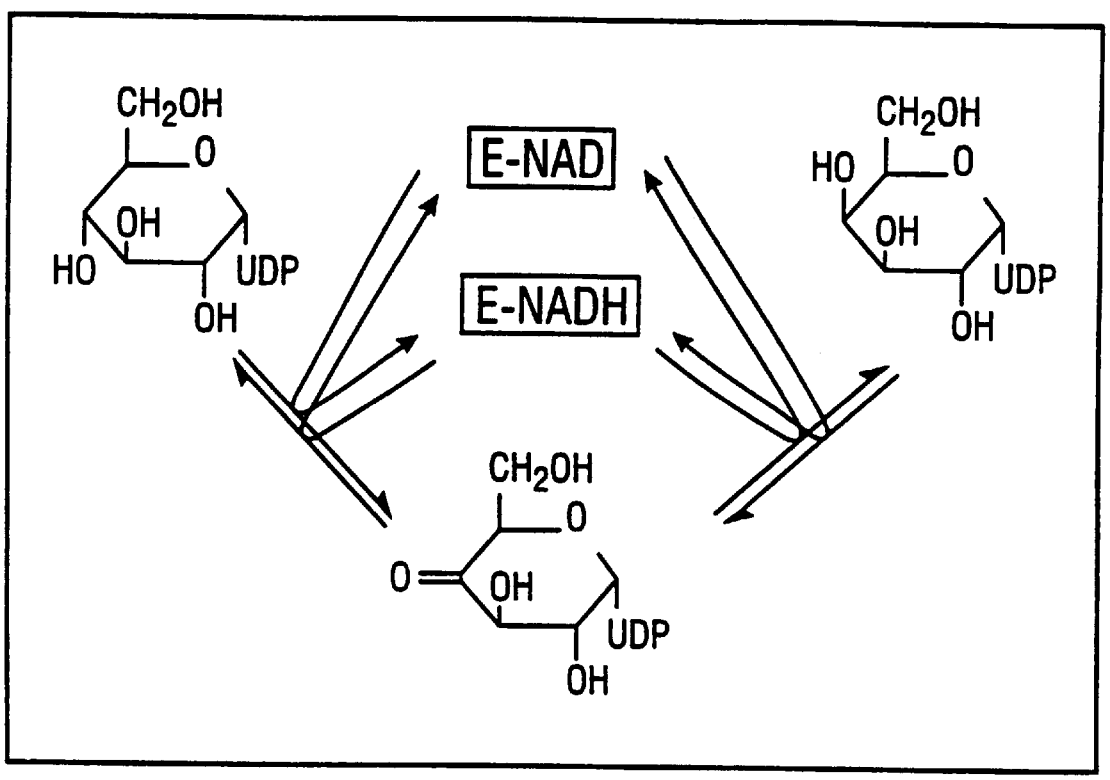
FIG. 4 shows a schematic drawing of the mechanism of the UDP-Glc 4-epimerase reaction.
Figure 5:
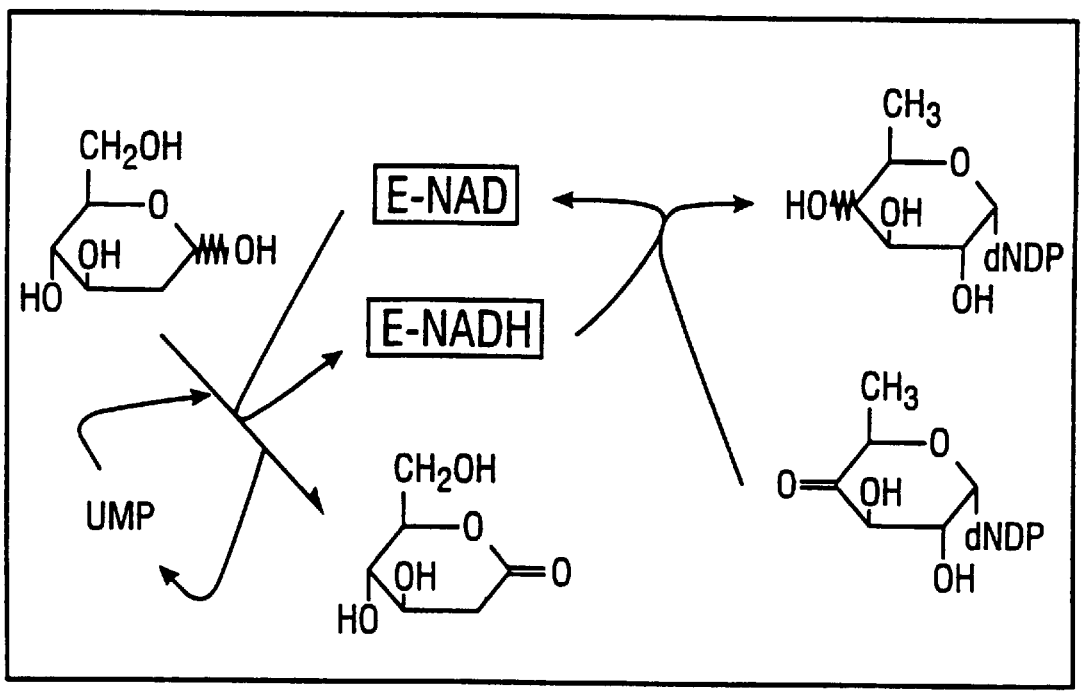
FIG. 5 shows a schematic drawing of a reactivation of the epimerase with DNDP-6-deoxy-D-xylo-4-hexulose according to the present invention.
Figure 6:
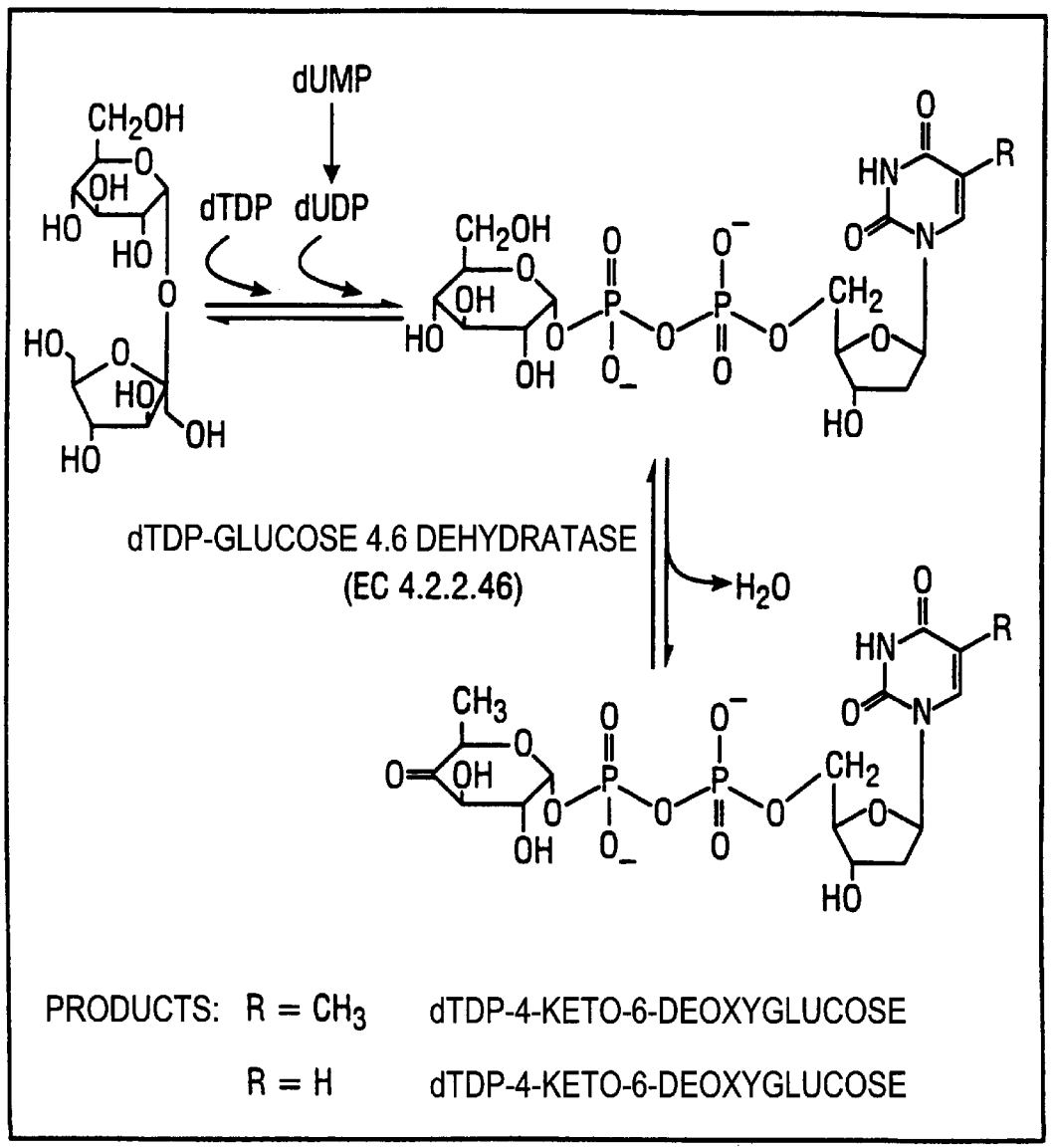
FIG. 6 shows a schematic drawing of enzymic synthesis of nucleoside deoxysugars according to the present invention.
Figure 10:
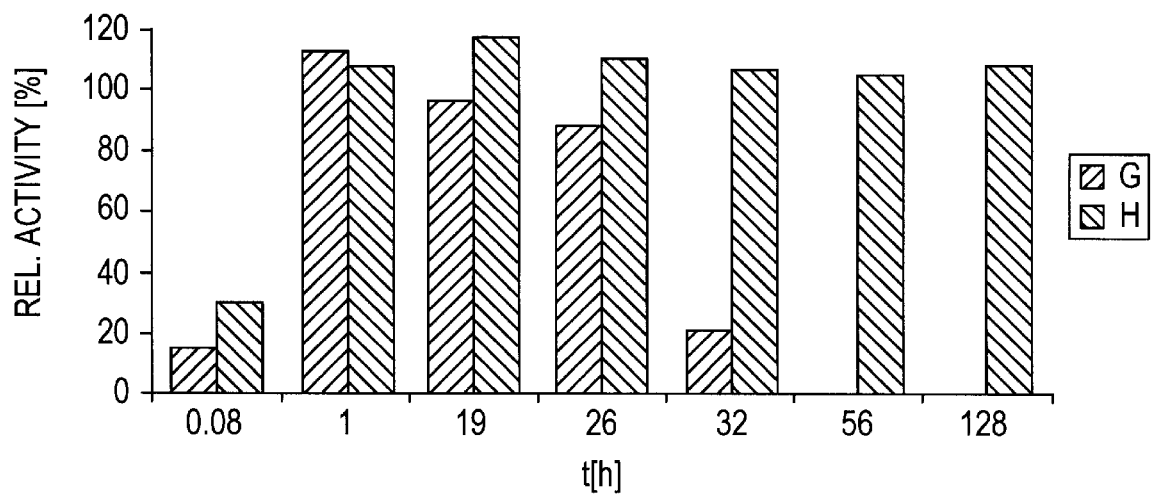
FIG. 10 shows long-term stability of the epimerase following activation in accordance with the present invention.

Investigations into the stability of UDP-Glc 4'-epimerase showed that the yeast epimerase is inactivated in the presence of UDP-glucose and UDP-galactose (donor for the galactosyl transferase) and in the presence of various acceptors (Glc, 2-deoxyglucose, 5-thioglucose and n-octylglucopyranoside). This is a problem which occurs generally when the epimerase is used for the in-situ regeneration of UDP-galactose. In subsequent experiments, we were now able to demonstrate that dUDP-6-deoxy-D-xylo-4-hexulose and dTDP-6-deoxy-D-xylo-4-hexulose, in particular, can be used to reactivate the UDP-Glc 4'-epimerase (FIG. 5).

dUDP-6-deoxy-D-xylo-4-hexulose and dTDP-6-deoxy-D-xylo-4-hexulose are formed from dUDP-glucose and dTDP-glucose using dTDP-glucose 4,6-dehydratase [EC 4.2.1.46] as the catalyst (Zarkowsky et al. J. Biol. Chem. 244, 4750 (1969)).

dTDP-6-deoxy-D-xylo-4-hexulose is an intermediate in the pathway for the biosynthesis of dTDP-L-Rhamnose. The enzymatic synthesis and isolation of this substance has been described by Marumo et al. (Eur. J. Biochem. 204, 539 (1992)). While dUDP-Glc cannot be obtained commercially, it has been synthesized in analytical quantities by Melo et al. (J. Biol. Chem. 240, 398 (1965)) employing Pseudomonas aeruginosa dTDP-Glc pyrophosphorylase. dUDP-6-deoxy-D-xylo-4-hexulose and dTDP-6-deoxy-D-xylo-4-hexulose can be prepared from dUMP and dTDP, respectively, using the synthetic potential of sucrose synthase (FIG. 6).

dUDP-6-deoxy-D-xylo-4-hexulose was then used for the first time to reactivate the epimerase in the synthesis of N-acetyllactosamine (LacNAc). The activity of the epimerase was monitored over a period of 128 h. Addition of 1 mM dUDP-6-deoxy-D-xylo-4-hexulose resulted in rapid activation of the epimerase, with the activation being stable over the period of observation (FIG. 10).

Further improvement of the proposed process is achieved by using the repetitive-batch process (U. Kragl et al., Tetrahedron 4, 1193–1202 (1993)). In this process, the substrates are reacted in an ultrafiltration cell having a YM10 membrane in the presence of sucrose synthase, galactosyl transferase, epimerase and dUDP-6-deoxy-D-xylo-4-hexulose. After the reaction has come to an end, the product solution is filtered off through the ultrafiltration membrane, with the enzymes being retained. The reaction can be repeated several times by adding fresh substrate solution without it being necessary to meter in further enzyme. As a result, the native enzymes can be used repeatedly for the synthesis without any immobilization. In this context, the reactivation of the epimerase ensures that optimum use is made of the repetitive-batch process for economically synthesizing LacNAc and its analogs.

EXAMPLES

Example 1

Synthesis of dUDP-6-deoxy-D-xylo-4-hexulose starting from dUDP-Glc

Figure 9:
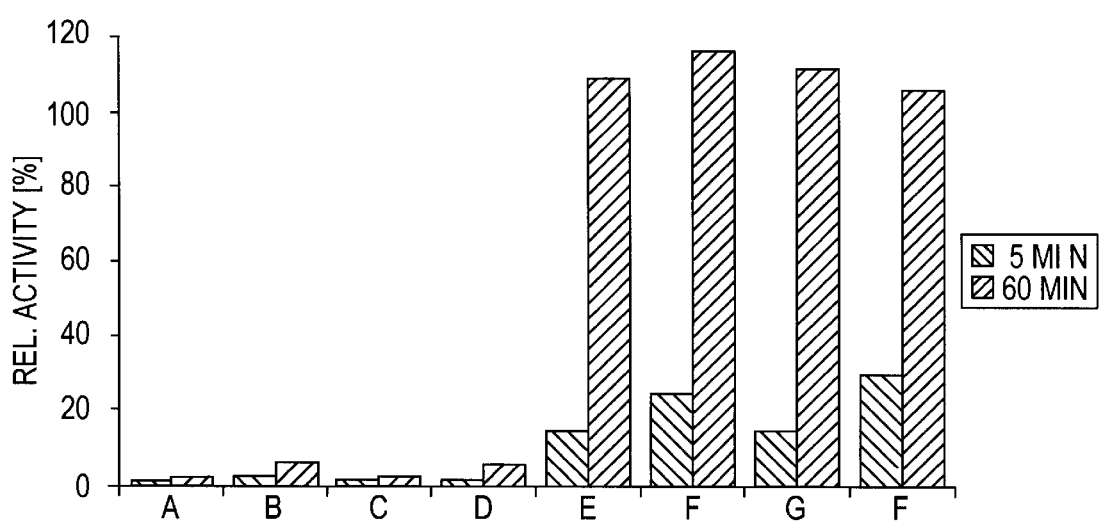
FIG. 9 shows a graph of reactivation of the epimerase in accordance of the present invention.

Synthesis Mixture
  20.1 mg of dUDP-Glc (approx. 10 mM, see 1.2.4)
  1920 µl of Hepes-NaOH (200 mM, pH 7.2, 1 mM DTT, 500 mM sucrose, 25 mM KCl, 1 mg/ml BSA)
  80 µl of dTDP-D-Glc 4,6-dehydratase (1.48 U, crude extract)
  Incubation at 30° C.; incubation time: 4 h After 4 h, it was no longer possible to detect any dUDP-Glc by HPLC (FIG. 9). The product was successfully employed to reactivate the epimerase. dTDP-6-deoxy-D-xylo-4-hexulose was synthesized under analogous experimental conditions. In this case, the reaction was complete after 1 h.

Example 2

Synthesis of dUDP-6-deoxy-D-xylo-4-hexulose starting from dUMP

Synthesis Mixture
  V=3 ml 4 mM dUMP (Na salt, Sigma®), 4 mM PEP (CHA salt, Biomol®), 0.8 mM MgCl$_2$, 0.12 mM ATP (Na salt, Sigma®), 500 mM sucrose, 6 S.Syn. (2 U/ml), 60 U of pyruvate kinase (20 U/ml), 3 U of NMPK (1 U/ml), 15 U of dTDP-D-Glc 4,6-dehydratase (5 U/ml),
  Buffer: Tris-HCl (100 mM, pH 7.2, 3 mM DTT, 1 mg/ml bovine serum albumin (BSA), 50 mM KCl)
  Incubation temperature: 25° C.
  69.3% of the product had formed after an incubation time of 4 h.

Example 3

Synthesis of LacNAc by the repetitive-batch process

The aim of using the repetitive-batch process is to achieve a substantial increase in the productivity of the synthesis.
Optimal Synthesis of LacNAc
  1 mM UDP-Glc, 1 mM MnCl$_2$, 10 mM GlcNAc, 500 mM sucrose, 0.05 U/ml GalT, 0.2 U/ml epimerase, 0.4 U/ml sucrose synthase, buffer: 200 mM Hepes-NaOH, pH 7.2, 0.1% BSA, 1 mM DTT

| Incubation temperature: | 30° C. |
|---|---|
| Conversion: | 100% |
| Number of cycles: | 10 |
| Productivity: (S-T Y = Space-time yield) | 200 mM*ml/U S-T Y: 3.8 g/l*d |
| Synthesis mixture: | 1 ml of the optimized LacNAc mixture |

After 12 hours at 30° C., approx. 750 μl of the product solution were centrifuged off using a Zentricon® YM 10. Diafiltration of the remaining approx. 250 μl with buffer without bovine serum albumin (BSA).

The enzyme solution was transferred to Eppendorf® cups and made up to 1 ml with substrate solution. Samples are in each case taken at the beginning and after the end of the reaction.

Results

Figure 7:
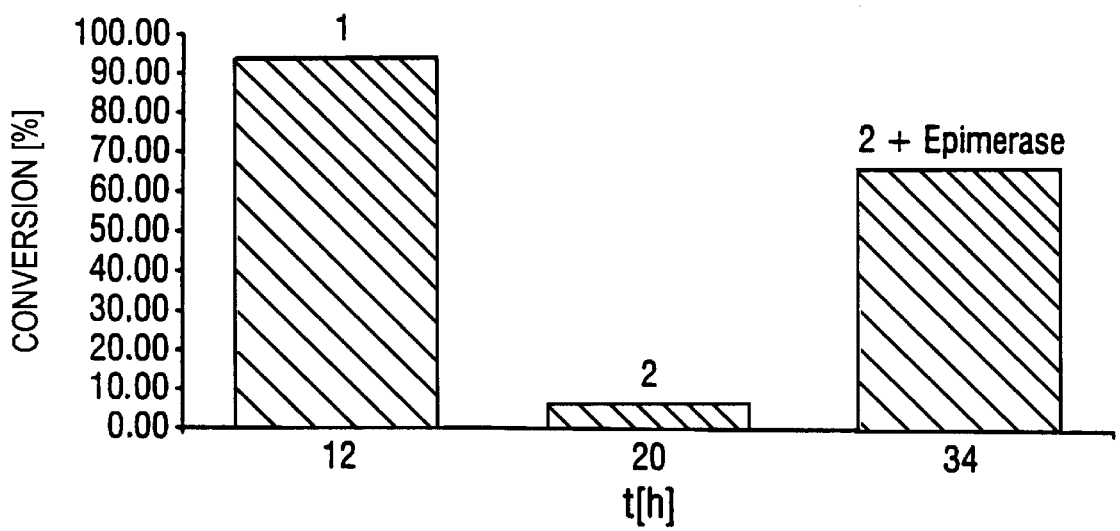
FIG. 7 shows a bar graph of the synthesis of LacNAc by the repetitive-batch process without reactivating the epimerase according to the present invention.

The results in FIG. 7 show that the epimerase was no longer active after a reaction time of 12 h and after centrifuging through the YM10 membrane. Because of this result, the stability of the epimerase in the buffer system employed was investigated in more detail.

Example 4

Investigation of the stability of the epimerase

Inactivation of the epimerase by sugar in the presence of UMP

The epimerase was incubated in the buffer system employed and the activity of the enzyme was monitored over a period of 8 hours.

Experimental Conditions

Buffer Solutions

A: 200 mM Hepes pH 7.2, 1 mM DTT, 1 mg/ml BSA
B: 200 mM Hepes pH 7.2, 1 mM DTT, 1 mg/ml BSA, 500 mM sucrose Mixture A. Buffer solution A
B. Buffer solution A, 0.1 mM UMP
C. Buffer solution B
D. Buffer solution B, 0.1 mM UMP in each case containing 0.25 mg/ml epimerase Incubation temperature: 30° C.
Activity test: (Fukusawa et al., J. Biol. Chem. 255, 2705–2707 (1980))

| 893 μl of 100 mM glycine buffer, pH 8.8 |
|---|
| 20 μl of 5 mM UDP-Gal |
| 20 μl of 50 mM NAD |
| 33.3 μl of UDP-Glc dehydrogenase (2 U/ml) |
| 33.3 μl of epimerase |

Temperature: 25° C.
Measurement at 340 nm

Results

Figure 8:
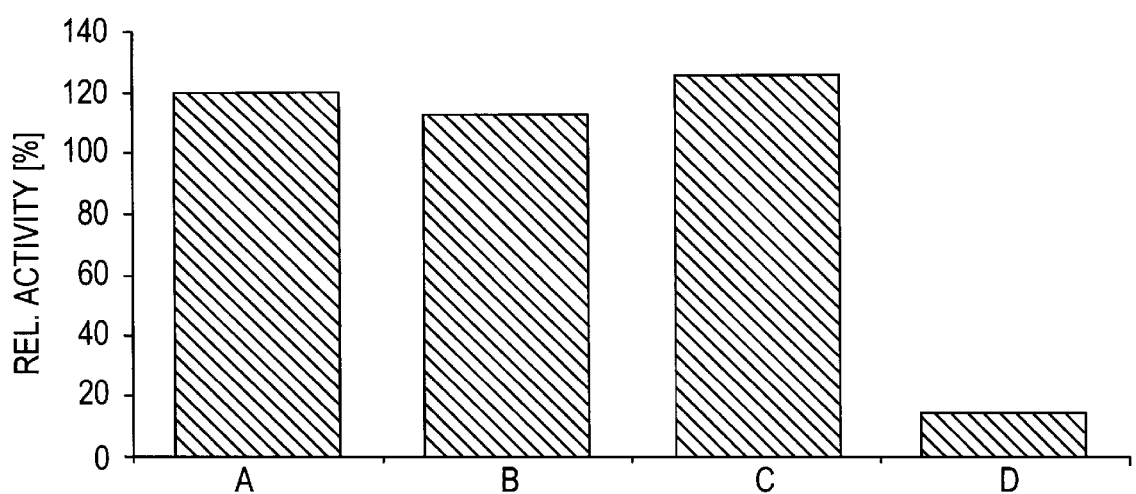
FIG. 8 shows a bar graph of an inactivation of the epimerase by sugar and UMP in the buffer system employed according to the present invention.

FIG. 8 summarizes the results and makes it clear that the epimerase is inactivated in the presence of sucrose, or its cleavage products, glucose and fructose, and UMP.

Example 5

Inactivation of the epimerase in the presence of various acceptors and donors of GalT In order to examine the thesis that the inactivation of the epimerase can occur in association with many applications, the stability of the epimerase was tested in the presence of various donors and acceptors of GalT. The results are summarized in Table 1.

TABLE 1

| | Rel. activity of the epimerase in the presence of various donors and acceptors of GalT | | | | |
|---|---|---|---|---|---|
| Incubation time | 2h | 7h | 8h | 24h | R |
| Donors: | | | | | |
| P*, 1 mM UDP-Glc pH 7.2 | 80.7 | — | 80.7 | 58.3 | 137 |
| P*, 1 mM UDP-Glc pH 8.0 | 83.3 | — | 67.9 | 35.5 | 128 |
| Acceptors: | | | | | |
| P, 50 mM GlcNAc | 93.6 | 97.5 | — | — | — |
| P, 50 mM 2-Deoxyglc | 20.7 | — | — | — | — |
| P, 50 mM Glc | 15.8 | — | — | — | — |
| P, 50 mM Thioglc | 87.9 | 34.3 | — | — | — |
| P, 50 mM n-Octylglucopyranoside | 86.1 | 75.6 | 29.3 | — | — |

P: 200 mM Hepes-NaOH, pH 7.2, 1 mM DTT, 1 mg/ml BSA, 25 mM KCl containing 0.1 mM UMP
P*: Buffer without UMP
R: Activity following reactivation of the epimerase with dTDP-6-deoxy-D-xylo-4-hexulose (c = 0.1 mM)

The results in Table 1 make it clear that the epimerase is inactivated in the presence of various acceptors of GalT (Glc, thioglc, 2-deoxyglc and n-octylglucopyranoside) in the presence of UMP and UDP-Gal or UDP-Glc. consequently, this is a problem which occurs generally when the epimerase is used to regenerate UDP-Gal in situ.

Example 6

Reactivation of the epimerase

Both dUDP-6-deoxy-D-xylo-4-hexulose and dTDP-6-deoxy-D-xylo-4-hexulose, and also 6-deoxyglucosone, galactosone, allosone and glucosone, were used for reactivating the epimerase.

Experimental Conditions

1. Synthesis of dUDP-6-deoxy-D-xylo-4-hexulose and dTDP-6-deoxy-D-xylo-4-hexulose (see Example 1)
2. Inactivation of the epimerase
   Incubation mixture:
   50 mM galactose
   0.1 mM UMP
   0.25 mg/ml epimerase
   Buffer:
   20 mM Hepes-NaOH, pH 7.2
   1 mM dithiothreitol
   1 mg/ml bovine serum albumin (BSA)
   25 mM KCl
   After an incubation period of 2 h at 30° C., the measured activity of the epimerase was 3%.
3. Activation of the epimerase
   Incubation mixture:
   160 μl of inactivated epimerase
   40 μl of activator (different concentrations)

The results of the epimerase activation are given in FIG. 9. In samples G and H, the activity of the epimerase was monitored over a period of 128 h. The results are summarized in FIG. 10.

The results show that a rapid and long-lasting activation of the epimerase can be achieved by adding dTDP-6-deoxy-D-xylo-4-hexulose and dUDP-6-deoxy-D-xylo-4-hexulose. The deactivation velocity is concentration-dependent, so that, at a concentration of 0.1 mM, a renewed inactivation of the epimerase can be observed after 32 hours due to the galactose and UMP which are still present in the mixture.

Example 7

Synthesis of LacNAc in the repetitive-batch process when epimerase is reactivated Material and Methods 183 mg of UDP-Glc (Na salt, Sigma®, 1 mM), 597 mg of GlcNAc (10 mM), 46.2 mg of $MnCl_2$ (1 mM), 46.2 g of sucrose (500 mM), 1.25 U of GalT (0.05 U/ml), 5 U of epimerase (0.2 U/ml), 10 U of sucrose synthase (0.4 U/ml) and 25 mg of BSA in 200 mM Hepes-NaOH (1 mM DTT, 25 mM Kcl, pH 7.2) were used for the LacNAc synthesis. The reaction volume in the batch was ten times 25 ml and one times 20 ml (total volume: 270 ml). 250 $\mu$l (batch mixture 11:200 $\mu$l) of the synthesis mixture (Example 1) (approx. 0.1 $\mu$M dUDP-6-deoxy-D-xylo-4-hexulose) were in each case added for the purpose of reactivating the epimerase. The diafiltration was carried out in a 50 ml Amicon® cell having a YM10 membrane. The reaction mixture was made up to a volume of 50 ml with buffer and concentrated down to 25 ml three times. In the last filtration, the volume was reduced to 20 ml and the following reaction was started by adding 5 ml of substrate solution. After the substrate solution had been added, the reaction mixture was sterilized by filtration. The filtrate was stored at $-20°$ C.

Incubation time: 21–30 h

Incubation temperature: 30° C.

Figure 11:
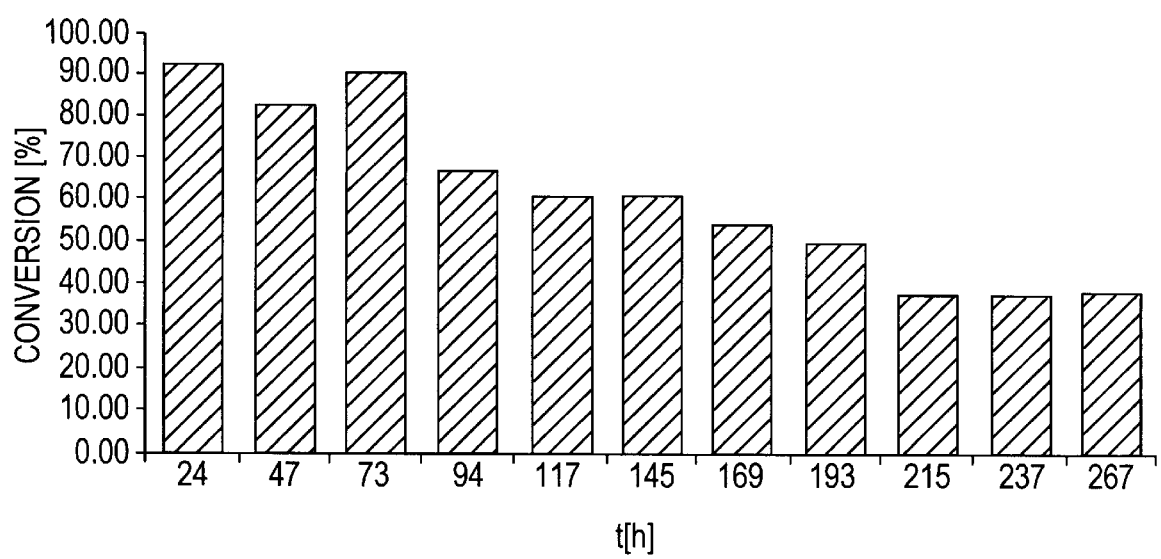
FIG. 11 shows synthesis of LacNAc in a repetitive batch with reactivation of the epimerase in accordance with the present invention.

The course of the synthesis is depicted in FIG. 11. Over 11 days, 597 mg of GlcNAc (2.7 mmol) were converted into 594 mg of LacNAc (1.55 mmol), corresponding to an average yield of 57.4%.

Example 8

Product purification: LacNAc

1. Cleaving the sucrose with invertase 25,000 U/ml invertase (Sigma®, *Sacch. cerevisiae*) in buffer B (3.3.1), preincubated at 45° C. for 2 h;

Addition of 10 $\mu$l of invertase/ml of product solution incubation at 45° C. and regular checking of the reaction using a polarimeter After 120 minutes, the protein was separated off using a YM10 membrane.

The filtrate was divided into 5 batches.

2.) Sugar separation using a calcium column

Column: AG50W-X8 (5×35 cm) in Ca form, eluent: double distilled water,

Flow rate: 0.5 ml/min.

Prior to sample application, the sample was concentrated down to approx. 30 ml on a rotary evaporator (20–25 mbar, 30–35° C.).

After the sugars had been separated, the fractions which contained LacNAc were pooled.

3.) Ion exchange chromatography on Dowex® 1×2 Cl⁻ (100–200 mesh)

Column: 2.6×26.5 cm, flow rate 3.5 ml/min, eluent: double distilled water

The pH of the sample was adjusted to 8.5. The fractions which contained LacNAc were pooled and the pH was adjusted to 7.0.

4.) Gel filtration using a $P_2$ column

Column: Biorad® $P_2$ column (2.6×82 cm), eluent: double distilled water,

Flow rate: 0.5 ml/min.

The fractions which contained LacNAc were pooled. Batches 1–5 were combined.

5.) The remnants of Hepes which were still present were separated off by means of a further ion exchange chromatography (see 3.).

6.) The product was to a large extent desalted by means of two gel filtration runs (see 4.)

7.) In order to increase the purity of the product, some of the GlcNAc and salt which was still present was removed using a Ca column (see 2.).

8.) The product solution was concentrated on a rotary evaporator and then freeze-dried.

| | |
|---|---|
| Weight after synthesis: | 594 mg |
| Weight after purification: | 356 mg (59.9%) |

Example 9

Syntheses using various acceptors and donors of GalT

The following donors and acceptors have so far been employed in the LacNAc cycle in subsequent syntheses:

Donors: dUDP-Glc

Acceptors: 2-deoxy-D-glucose, 5-thio-D-glucose, Glc, n-octylglucopyranoside, n octylthioglucopyranoside, 6-aminohexyl-N-acetylglucosaminide.

Varying the donor

Experimental conditions: optimized LacNAc mixture containing 0.05 U/ml GalT, with the epimerase being reactivated with 1 mM dUDP-Glc.

Analysis: HPLC method for LacNAc

Results 12.5% LacNAc was formed after 17 hours in the synthesis containing 0.05 U/ml GalT.

Synthesis of lactose analogs

Experimental conditions:

| | |
|---|---|
| Synthesis mixture: | optimized synthesis mixture containing 0.1 mM dTDP-6-deoxy-D-xylo-4-hexulose and 0.1 mg/ml α-lactalbumin |
| Acceptors: | 2-deoxyglc; thioglc, Glc, n-octylglucopyranoside and n-octylthioglucopyranoside |
| Blank sample: | Synthesis mixture without acceptor |

HPLC analysis for 2-deoxyglc, thioglc and Glc

Column: Aminex HPX-87C at 85° C., flow rate: 0.5 ml/min

Eluent: double distilled water, detector:

a) UV-Vis 205 nm b) chiralyzer

TLC analysis for n-octylglucopyranoside, n-octylglucopyranoside and 6-aminohexyl-N-acetylglucosaminide Mobile solvent: 85:12:3 (n-propanol:HAC:$H_2O$)

Spray: 50% methanolic $H_2SO_4$

Results

The results showed that lactose was formed in all the syntheses. Substantially more lactose is formed in the synthesis using Glc as the acceptor than in the other syntheses.

Whereas thioglucose, n-octylthioglucopyranoside and n-octylglucopyranoside are converted into the respective disaccharides, conversion of 2-deoxyglc cannot at present be detected.

Example 11

Preparative syntheses

1. Preparative synthesis of N-octyl-4-β-D-galactopyranosyl-D-glucopyranoside and 4-O-β-galactopyranosyl-D-2-deoxyglucose 41 mg of UDP-Glc (Na salt, Sigma®, 1 mM), 175 mg of n-octylglucopyranoside (Südzucker, 10 mM) or 97 mg of 2-deoxyglc (Fluka®, 10 mM), 12 mg of $MnCl_2$ (1 mM), 10.3 of sucrose (500 mM), 1.2 of GalT (0.06 U/ml), 4 U of epimerase (0.2 U/ml), 8 U of sucrose synthase (0.4 U/ml), 6 mg of lactalbumin (0.1 mg/ml) and 20 mg of BSA, in 200 mM Hepes-NaOH (1 mM DTT, 25 mM KCl, pH 7.2), were employed for the synthesis. The reaction volume was three times 20 ml (total volume: 60 ml). 200 μl of the synthesis mixture (Example 1) (approx. 0.1 mM dTDP-6-deoxy-D-xylo-4-hexulose) were added daily in order to reactivate the epimerase. Diafiltration was carried out in a 50 ml Amicon® cell having a YM10 membrane.

Incubation time: 2 days per mixture

Incubation temperature: 30° C.

Product Purification

1. N-Octyl-4-β-D-galactopyranosyl-D-glucopyranoside

The product solution was passed in fractions (5 fractions) through 5 Sep-Pack C-18 reverse phase columns supplied by Waters® (Mississauga, Ont., Canada) (Palcic et al., Glycoconjugate J. 5. 49–63 (1988). Preparation of the columns: rinsing with 10 ml of methanol and 20 ml of double distilled water, application of the sample, rinsing the column with 20 ml of double distilled water, and elution of the product and starting material with 10 ml of methanol.

The methanol was stripped off on a rotary evaporator at 30° C. and 120 mbar and the sugars were dissolved in double distilled water. The disaccharides were separated from the monosaccharide using a P2 column (2.6×82 cm, flow rate: 0.5 ml/min, double distilled water)

Weight: 58.3 mg, yield: 21.4%.

2. 4-O-β-Galactopyranosyl-D-2-deoxyglucose

The product was purified in analogy with the purification of LacNAc. The TLC method described for N-octyl-4-β-D-galactopyranosyl-D-glucopyranoside was used for the analysis. (weight: 53.4 mg≅28.7%.)

We claim:

1. A process for enzymically galactosylating monosaccharides and oligosaccharides, with in-situ regeneration of a nucleotide sugar or of a nucleoside diphosphate sugar, in the presence of sucrose synthase, β-1-4-galactosyl transferase and uridine diphosphate-glucose 4'-epimerase, wherein a deoxynucleoside diphosphate ketosugar, galactosone, allosone, glucosone or 6-deoxyglucosone is added to the reaction mixture as an activator of the uridine diphosphate-glucose 4'-epimerase.

2. A process for enzymically galactosylating monosaccharides and oligosaccharides, with in-situ regeneration of the nucleotide sugar, in the presence of sucrose synthase, β-1-4-galactosyl transferase and uridine diphosphate-glucose 4'-epimerase, wherein deoxyuridine diphosphate-6-deoxy-D-xylohexulose is added to the reaction mixture as an activator of the uridine diphosphate-glucose 4'-epimerase.

3. A process for enzymically galactosylating monosaccharides and oligosaccharides, with in-situ regeneration of the nucleotide sugar, in the presence of sucrose synthase, β-1-4-galactosyl transferase and uridine diphosphate-glucose 4'-epimerase, wherein deoxythymidine diphosphate-6-deoxy-D-xylohexulose is added to the reaction mixture as an activator of the uridine diphosphate-glucose 4'-epimerase.

4. The process as claimed in claim 1, wherein a ketosugar is employed as the activator.

5. The process as claimed in claim 1, wherein the concentration of the activator in the reaction mixture is from 0.01 to 20 mM.

6. The process as claimed in claim 1, wherein the concentration of the activator in the reaction mixture is from 0.1 to 1 mM.

7. The process as claimed in claim 1, wherein the process is carried out as a repetitive-batch process in an ultrafiltration cell.

\* \* \* \* \*